US012751903B2

(12) United States Patent
Bae et al.

(10) Patent No.: US 12,751,903 B2
(45) Date of Patent: Oct. 6, 2026

(54) WATER-IN-OIL COSMETIC COMPOSITION WITH MAXIMIZED FEELING OF MOISTURE

(71) Applicant: KOLMAR KOREA CO., LTD., Seoul (KR)

(72) Inventors: Su Jin Bae, Seoul (KR); Jin Young Kim, Seoul (KR); Jin Mo Kim, Seoul (KR); In Ki Hong, Seoul (KR)

(73) Assignee: KOLMAR KOREA CO., LTD., Seoul (KR)

(*) Notice: Subject to any disclaimer, the term of this patent is extended or adjusted under 35 U.S.C. 154(b) by 750 days.

(21) Appl. No.: 17/624,848

(22) PCT Filed: Sep. 8, 2021

(86) PCT No.: PCT/KR2021/012235

§ 371 (c)(1),
(2) Date: Jan. 5, 2022

(87) PCT Pub. No.: WO2022/092550

PCT Pub. Date: May 5, 2022

(65) Prior Publication Data

US 2022/0378674 A1 Dec. 1, 2022

(30) Foreign Application Priority Data

Oct. 30, 2020 (KR) ........................ 10-2020-0142800

(51) Int. Cl.

| | |
|---|---|
| ***A61K 8/25*** | (2006.01) |
| ***A61K 8/06*** | (2006.01) |
| ***A61K 8/34*** | (2006.01) |
| ***A61K 8/368*** | (2006.01) |
| ***A61K 8/37*** | (2006.01) |
| ***A61K 8/40*** | (2006.01) |
| ***A61K 8/41*** | (2006.01) |
| ***A61Q 17/04*** | (2006.01) |

(52) U.S. Cl.

CPC ................ *A61K 8/25* (2013.01); *A61K 8/064* (2013.01); *A61K 8/345* (2013.01); *A61K 8/368* (2013.01); *A61K 8/37* (2013.01); *A61K 8/40* (2013.01); *A61K 8/415* (2013.01); *A61Q 17/04* (2013.01); *A61K 2800/524* (2013.01); *A61K 2800/75* (2013.01)

(58) Field of Classification Search

CPC .......... A61K 8/25; A61K 8/064; A61K 8/345; A61K 8/368; A61K 8/37; A61K 8/40; A61K 8/415; A61K 2800/524; A61K 2800/75; A61Q 17/04

See application file for complete search history.

(56) References Cited

U.S. PATENT DOCUMENTS

| | | | | |
|---|---|---|---|---|
| 7,037,511 | B1 * | 5/2006 | Gers-Barlag | A61Q 17/005 424/59 |
| 2010/0233103 | A1 * | 9/2010 | Shirao | A61K 8/0245 424/59 |
| 2014/0127140 | A1 * | 5/2014 | Ferritto | C08G 65/2639 424/59 |
| 2017/0333301 | A1 * | 11/2017 | Yamaki | A61K 8/064 |
| 2019/0167559 | A1 | 6/2019 | Tadini D'Annolfo et al. | |

FOREIGN PATENT DOCUMENTS

| | | | | |
|---|---|---|---|---|
| JP | 10-120525 A | | 5/1998 | |
| JP | 2004-075620 A | | 3/2004 | |
| KR | 10-0722677 B1 | | 5/2007 | |
| KR | 10-2011-0058949 A | | 6/2011 | |
| KR | 10-2013-0049053 A | | 5/2013 | |
| KR | 10-2015-0124949 A | | 11/2015 | |
| WO | WO-2011047982 A2 | * | 4/2011 | A61K 8/606 |
| WO | WO-2019093199 A1 | * | 5/2019 | A61K 8/025 |

OTHER PUBLICATIONS

International Search Report for PCT/KR2021/012235 mailed Dec. 15, 2021 from Korean Intellectual Property Office.

* cited by examiner

*Primary Examiner* — Robert A Wax
*Assistant Examiner* — Olga V. Tcherkasskaya
(74) *Attorney, Agent, or Firm* — Revolution IP, PLLC

(57) ABSTRACT

The present invention relates to a water-in-oil cosmetic composition with maximized feeling of moisture and refreshment and, more particularly, to a water-in-oil cosmetic composition which includes organically modified clay minerals and polar oils containing at least one ester group having a specific content, so that the stability of emulsified particles is maintained without a separate emulsifier, thus reducing skin irritation during application and forming water drops to enhance visual aesthetics and maximize feeling of moisture and refreshment.

1 Claim, 1 Drawing Sheet

WATER-IN-OIL COSMETIC COMPOSITION WITH MAXIMIZED FEELING OF MOISTURE

TECHNICAL FIELD

The present invention relates to a water-in-oil cosmetic composition with maximized feeling of moisture and refreshment and, more particularly, to a water-in-oil cosmetic composition which includes organically modified clay minerals and polar oils containing at least one ester group having a specific content, so that the stability of emulsified particles is maintained without a separate emulsifier, thus reducing skin irritation during application and forming water drops to enhance visual aesthetics and maximize feeling of moisture and refreshment.

BACKGROUND ART

Cosmetics have the function of protecting the skin from external factors such as ultraviolet rays and environmental pollution and delaying aging. Most cosmetics are present in a state in which an aqueous phase is dispersed in an oil phase or an oil phase is dispersed in an aqueous phase. At this time, the use of an emulsifier (surfactant) is essential to maintain a stable dispersion state.

The emulsifier is a molecule having an amphiphilic structure consisting of a hydrophilic group which is easy to be compatible with water and a hydrophobic group which is easy to be compatible with oil. The emulsifier is located at an interface between the oil phase and the aqueous phase to lower an interfacial tension, and forms an oil/water interface at the phase boundary to prevent particles from coalescing with each other.

Emulsifiers may be classified according to various properties such as use, performance, chemical structure, etc. In general, the emulsifiers are divided into ionic and nonionic characters according to their dissociation properties in water. Ionic emulsifiers that dissociate when dissolved in water are further divided into anionic, cationic and amphoteric emulsifiers. A representative example of anionic emulsifiers is a fatty acid salt soap, and a representative example of cationic emulsifiers is a quaternary ammonium compound. In addition, nonionic emulsifiers that do not dissociate into ions when dissolved in water have various hydrophilic parts such as glycerol, polyglycerol, sorbitan, polyoxyethylene glycol, etc., and have an ester bond or an ether bond with a lipophilic part such as fatty acid, fatty alcohol or the like.

Many commercially available emulsifiers are used with an approval for safety. Nevertheless, emulsifiers cause an interfacial action even in dermal cells and thus destroy a phospholipid layer, thereby causing skin irritation or allergies. Loss of the lipid layer weakens a barrier and increases skin permeability. A barrier with increased permeability easily loses moisture, resulting in dull and dry skin. In addition, penetration of foreign substances is facilitated, resulting in a sensitive skin reaction such as an allergy.

General water-in-oil cosmetics are less sticky and have good lasting power, but have a lower feeling of moisture and a higher oily feeling compared to oil-in-water cosmetics. Raw materials such as powder, silicone gum, etc., are used to make up the oily feeling, but it is difficult to compensate for the lack of feeling of moisture. As such, various attempts have been made to increase the feeling of moisture in the water-in-oil type, but it is difficult to maintain the stability of the formulation, which is thus hardly commercialized into products that consumers can purchase and use.

Thus, there is a need for the water-in-oil cosmetic composition in which the stability of emulsified particles is maintained without a separate emulsifier, so as to form water drops while minimizing skin irritation during application, thereby enhancing visual aesthetics and maximizing feeling of moisture and refreshment.

DISCLOSURE

Technical Problem

An object of the present invention is to provide a water-in-oil cosmetic composition with maximized feeling of moisture and refreshment, which includes organically modified clay minerals and polar oils containing at least one ester group having a specific content, so that the stability of emulsified particles is maintained without a separate emulsifier, thus reducing skin irritation during application and forming water drops to enhance visual aesthetics and maximize feeling of moisture and refreshment.

However, the technical objects to be achieved by the present invention are not limited to those mentioned above, and other objects that are not mentioned will be clearly understood by those skilled in the art from the following description.

Technical Solution

According to one embodiment of the present invention, there may be provided a water-in-oil cosmetic composition which contains organically modified clay minerals and oils, in which the oils are polar oils containing at least one ester group.

In the present invention, a weight ratio of organically modified clay minerals and oils may be 1:20 to 1:80.

In the present invention, the skin active ingredients may be at least one selected from the group consisting of UV blocking ingredients, including ethylhexylmethoxycinnamate, homosalate, diethylamino hydroxybenzoyl hexyl benzoate, octocrylene, ethylhexyltriazone, bisethylhexyloxyphenol methoxyphenyltriazine, polysilicon-15, tris-biphenyl triazine, ethylhexyl salicylate, benzophenone-3, avobenzone, phenylbenzimidazole sulfonic acid, isoamyl p-methoxycinnamate, methylenebis-benzotriazolyltetramethylbutylphenol, diethylhexyl butamido triazone, terephthalylidene dicamphor sulfonic acid and salts thereof, drometrizole, digalloyl trioleate, 4-methylbenzylidene camphor, menthyl anthranilate, benzophenone-4, benzophenone-8, cinoxate, ethylhexyl dimethyl para-aminobenzoic acid (PABA), titanium dioxide, zinc oxide, disodium phenyl dibenzimidazole tetrasulfonate and drometrizole trisiloxane; oil-soluble vitamins and derivatives thereof, oil-soluble bioactive ingredients including idebenone, alpha-bisabolol, and oil-soluble extracts of *Glycyrrhiza glabra* (common name: licorice); water-soluble vitamins and derivatives thereof and water-soluble bioactive ingredients and natural extracts including arbutin and adenosine.

In the present invention, the organically modified clay minerals may be at least one selected from the group consisting of disteardimonium hectorite, stearalkonium hectorite, quaternium-18 hectorite, quaternium-18 bentonite, quaternium-18/benzalkonium bentonite, quaternium-90 bentonite and stearalkonium bentonite.

In the present invention, the polar oils including at least one ester group may be at least one selected from the group consisting of dibutyl adipate, propylene glycol dicaprylate, propylene glycol dicaprylate/dicaprate, C12-15 alkylbenzoate, propylheptyl caprylate, ethylhexyl palmitate, coco-caprylate/caprate, isotridecyl isononanoate, diisopropyl sebacate, cetearyl isononanoate, isopropyl palmitate, butyloctylsalicylate, butylene glycol dicaprylate/dicaprate, diisopropyl adipate and isononyl isononanoate.

Advantageous Effects

The water-in-oil cosmetic composition provided in the present invention does not include a separate emulsifier while including organically modified clay minerals and polar oils containing at least one ester group having a specific content, and thus can minimize the degree of irritation to the skin when applied.

In addition, the cosmetics containing the water-in-oil type cosmetic composition of the present invention is in the form of separate cosmetics without viscosity before shaking to mix, but is transformed into a formulation having a specific viscosity by shaking to mix, and the aqueous phase particles, which are in an internal phase, are united when applied to the skin, and thus water drops can be formed like dew, enhancing visual aesthetics and maximizing feeling of moisture and refreshment. Furthermore, the particle size may become uniform during shaking to mix and the particles may be evenly applied to secure dispersion stability.

BEST MODE

Figure 1:
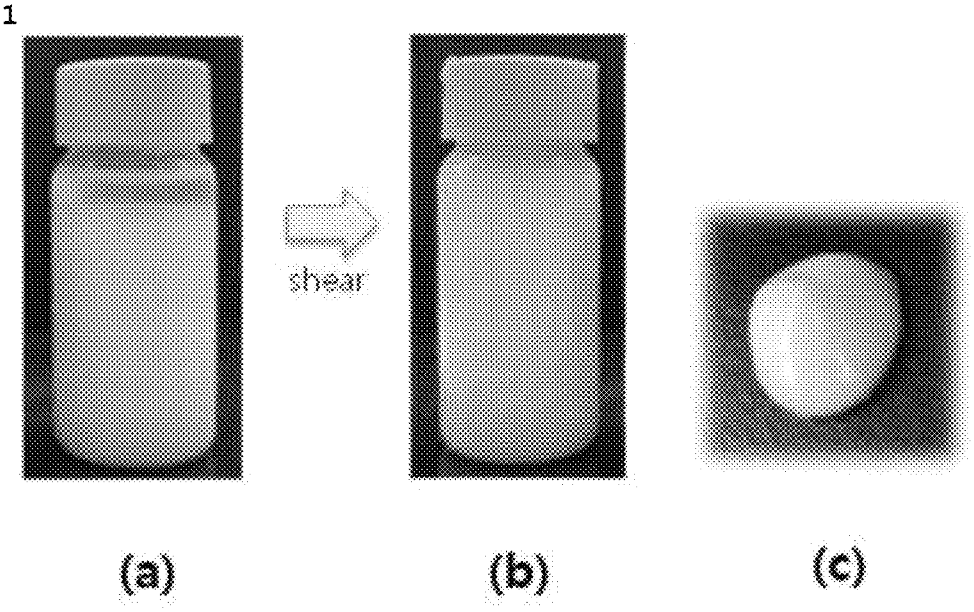
FIG. 1 is a photographic view showing the water-in-oil cosmetics of the present invention before (a) and after (b) shaking, and a photographic view showing the cosmetics discharged (c) after shaking.

According to one embodiment of the present invention, there may be provided a water-in-oil cosmetic composition which contains organically modified clay minerals and oils, in which the oils are polar oils containing at least one ester group.

MODE FOR INVENTION

According to one embodiment of the present invention, there may be provided a water-in-oil cosmetic composition which contains organically modified clay minerals and oils, in which the oils are polar oils containing at least one ester group.

In the present invention, the skin active ingredient is a functional ingredient that can effectively act on the skin while enhancing affinity with the skin, and it is possible to use any of UV protection ingredients, whitening ingredients, anti-wrinkle functional ingredients, antioxidant ingredients, moisturizing ingredients, antibacterial ingredients, etc.

The UV blocking ingredients may be at least one selected from the group consisting of ethylhexylmethoxycinnamate, homosalate, diethylaminohydroxybenzoylhexylbenzoate, octocrylene, ethylhexyltriazone, bisethylhexyloxyphenol methoxyphenyl triazine, polysilicone-15, tris-biphenyl triazine, ethylhexyl salicylate, phenylbenzimidazole sulfonic acid, isoamyl p-methoxycinnamate, methylenebis-benzotriazolyl tetramethylbutylphenol, diethylhexyl butamido triazone, terephthalylidene dicamphor sulfonic acid and salts thereof, drometrizole, digalloyl trioleate, 4-methylbenzylidene camphor, menthyl anthranilate, avobenzone, benzophenone-3, benzophenone-4, benzophenone-8, cinoxate, ethylhexyl dimethyl PABA, titanium dioxide, zinc oxide, disodium phenyl dibenzimidazole tetrasulfonate, and drometrizole trisiloxane, but are not limited thereto.

Besides, other skin active ingredients may include oil-soluble vitamins and derivatives thereof, oil-soluble bioactive ingredients containing idebenone, alpha-bisabolol and oil-soluble Licorice(Glycyrrhiza) extracts, water-soluble vitamins and derivatives thereof, water-soluble bioactive ingredients containing arbutin and adenosine and natural extracts, etc., but are not limited thereto.

In the present invention, the organically modified clay minerals may serve to secure the stability of the swollen bentone gel network instead of the emulsifier. The organically modified clay minerals used herein may include organic smectites, for example, at least one selected from the group consisting of disteardimonium hectorite, stearalkonium hectorite, quaternium-18 hectorite, quaternium-18 bentonite, quaternium-18/benzalkonium bentonite, quaternium-90 bentonite and stearalkonium bentonite.

In the present invention, the content of the organically modified clay minerals may be 0.01 wt % or more, 0.1 wt % or more, 0.2 wt % or more, 0.3 wt % or more, 0.4 wt % or more, or 0.5 wt % or more, may be 2 wt % or less, 1.8 wt % or less, 1.5 wt % or less, 1.2 wt % or less, or 1.0 wt % or less, and may be, for example, 0.1 to 2 wt %, 0.2 to 1.8 wt %, or 0.3 to 1.0 wt % based on the total 100 wt % of the water-in-oil type cosmetics of the present invention. If the content of the organically modified clay minerals is out of the above range, the stability of the water-in-oil cosmetics may not be secured, or a water drop may not be formed when the cosmetics are applied to the skin.

In the present invention, the oils may be a polar oil containing at least one ester group, which may be at least one selected from the group consisting of dibutyl adipate, propylene glycol dicaprylate, propylene glycol dicaprylate/dicaprate, C12-15 alkylbenzoate, propylheptyl caprylate, ethylhexyl palmitate, coco-caprylate/caprate (a mixture of esters derived from coconut alcohol with caprylic and capric acids), isotridecyl isononanoate, diisopropyl sebacate, cetearyl isononanoate, isopropyl palmitate, butyloctylsalicylate, butylene glycol dicaprylate/dicaprate, diisopropyl adipate and isononyl isononanoate.

In the present invention, the polar oils containing at least one ester group may be included in an amount of 5 wt % or more, 10 wt % or more, 15 wt % or more, 20 wt % or more, 25 wt % or more, or 30 wt % or more, may be 50 wt % or less, 45 wt % or less, 40 wt % or less, 35 wt % or less, 30 wt % or less, 25 wt % or less, or 20 wt % or less, and may be, for example, 10 to 40 wt %, 15 to 40 wt %, or 20 to 40 wt % based on the total 100 wt % of the water-in-oil type cosmetics of the present invention. If the content of the polar oil is out of the above range, a water drop may not be formed when the cosmetics are applied to the skin or aqueous phase particles may be unevenly distributed.

In the present invention, the weight ratio of organically modified clay minerals and oils (that is, the oil is a polar oil containing at least one ester group) may be is 1:20 to 1:80, preferably 1:22 to 1:78, and even more preferably 1:25 to 1:75. If the weight ratio of organically modified clay minerals and oils is out of the above range, the size of water drops may become small when the cosmetics are applied to the skin, or the size of water drops may become too large to form a drop, thereby reducing the feeling of use and aesthetics.

In the present invention, the water-in-oil cosmetic composition may have an average particle size of emulsified particles of 20 to 60 μm.

The water-in-oil cosmetic composition of the present invention may maintain basic physical properties and quality in addition to the above-mentioned composition, if necessary, and may include ingredients widely known to and used by those skilled in the art as any conventional ingredient for preparation of each formulation.

According to another embodiment of the present invention, there may be provided a water-in-oil cosmetic composition which includes an oil phase containing skin active ingredients, organically modified clay minerals and oils; and an aqueous phase containing purified water.

The water-in-oil cosmetics containing the water-in-oil type cosmetic composition of the present invention may be in the form of separate cosmetics without viscosity before shaking to mix, but is transformed into a formulation having a specific viscosity by shaking to mix, and the aqueous phase particles, which are in an internal phase, may be united when applied to the skin, and thus water drops may be formed like dew, enhancing visual aesthetics and feeling of use. Furthermore, the particle size may become uniform during shaking to mix and the particles may be evenly applied to secure dispersion stability.

The water-in-oil cosmetics of the present invention may have a viscosity of 3,000 to 25,000 CPS, preferably 3,500 to 22,000 CPS, and more preferably 4,000 to 20,000 CPS after the formulation is modified by shaking to mix.

The water-in-oil cosmetic composition of the present invention may include an aqueous phase containing purified water. The content of the purified water may not be particularly limited, but the content may be adjusted so that the total amount of the water-in-oil cosmetic composition of the present invention may be 100 wt % (TO 100).

The aqueous phase included in the water-in-oil cosmetics of the present invention may contain a moisturizing agent to prevent moisture loss from the skin when applied to the skin, thereby providing a moisturizing effect.

According to another embodiment of the present invention, there may be provided a method for preparing a water-in-oil cosmetic composition, which includes mixing organically modified clay minerals and oils, in which the oils are polar oils containing at least one ester group.

In the method for preparing the water-in-oil cosmetics of the present invention, mixing of the oil phase and the aqueous phase may not be particularly limited, but may be performed, for example, by adding 30 to 50 wt % of the total aqueous phase ingredients to the oil phase ingredients while stirring to prepare the mixture, and then adding a residual amount of aqueous phase ingredients to the mixture.

Hereinafter, the present invention will be described in more detail through exemplary embodiments. These embodiments are provided only for the purpose of illustrating the present invention in more detail, and thus it will be apparent to those skilled in the art that the scope of the present invention is not limited thereto according to the gist of the present invention.

EXAMPLE

Cosmetics of Examples 1 to 10 and Comparative Examples 1 to 6 having the compositions of tables 1 to 3 below were prepared.

The cosmetics of above Examples or Comparative Examples were prepared by mixing the oil phase ingredients including skin active ingredients (sunscreen agent), oils (polar oils containing at least one ester group or non-polar oils) and organically modified clay minerals (hectorite), with aqueous phase ingredients including purified water, a moisturizer and a preservative. With respect to the prepared cosmetics, the physical properties, particle size, and feeling of use were measured by the following method.

Figure 2:
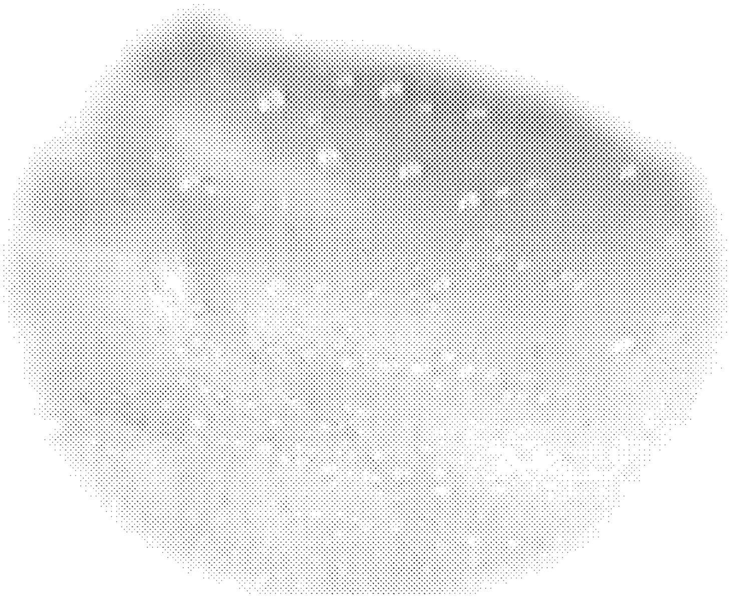
FIG. 2 is a photographic view showing the water-in-oil cosmetics of the present invention applied to the skin.

In addition, a photographic view showing the water-in-oil cosmetics of the present invention before (a) and after (b) shaking, and a photographic view showing the cosmetics discharged (c) after shaking are shown in FIG. 1. And, a photographic view showing the water-in-oil cosmetics of the present invention applied to the skin is shown in FIG. 2.

Presence of Emulsification (Particle Formation)

The presence or absence of macro-emulsified particles formed as a mark of the cosmetic composition was confirmed by observing the particles under an optical microscope using a polarizing filter.

Viscosity (Low Viscosity Thickener (LVT), No. 4*6 Rpm)

Viscosity was measured by shaking the contents 10 times to thoroughly mix the same, and then using a Brookfield Viscosmeter LVT with the spindle No. 4 and at a spin speed of 6 rpm.

TABLE 1

| | | Example | | | | |
|---|---|---|---|---|---|---|
| | | 1 | 2 | 3 | 4 | 5 |
| Polar oils containing an ester group | Dibutyl adipate | 26.000 | 12.000 | 8.000 | 32.000 | 36.000 |
| | Propylheptylcaprylate | 4.000 | 4.000 | 4.000 | 6.000 | 4.000 |
| | Coco-caprylate/caprate | — | — | — | — | — |
| Oil without an ester group | Dimethicone | — | — | — | — | — |
| | C15-19 alkanes | — | — | — | — | — |
| | Octyldodecanol | — | — | — | — | — |
| Emulsifier | Polyglyceryl-4 isostearate | — | — | — | — | — |
| | Polyglyceryl-5 polyricinoleate | — | — | — | — | — |
| Sunscreen agent | Ethylhexylmethoxycinnamate | — | 6.000 | — | — | — |
| | Homosalate | — | 4.000 | — | — | — |
| | Diethylaminohydroxy-benzoylhexylbenzoate | — | 3.000 | — | — | — |
| | Octocrylene | — | 1.000 | — | — | — |
| Hectorite | Disteardimonium hectorite | 0.500 | 0.500 | 0.500 | 0.500 | 0.500 |
| Ratio of hectorite: polar oil | | 1:60 | 1:60 | 1:24 | 1:76 | 1:80 |

TABLE 1-continued

| | | Example | | | | |
|---|---|---|---|---|---|---|
| | | 1 | 2 | 3 | 4 | 5 |
| Purified water | Purified water (thickening oil (TO) 100) | 63.90<br>0 | 63.90<br>0 | 81.90<br>0 | 55.90<br>0 | 53.90<br>0 |
| Moisturizer | Propanediol | 5.00 | 5.00 | 5.00 | 5.000 | 5.000 |
| Preservative | Caprylyl glycol | 0.1 | 0.1 | 0.1 | 0.1 | 0.1 |
| | Phenoxy ethanol | 0.50 | 0.50 | 0.50 | 0.50 | 0.50 |
| Formulation - emulsified or not (particle formation) | | O | O | O | O | O |
| Viscosity after shaking (LVT, No. 4*6 rpm) | | 10000 | 7500 | 16000 | 7500 | 5500 |

TABLE 2

| | | Example | | | | |
|---|---|---|---|---|---|---|
| | | 6 | 7 | 8 | 9 | 10 |
| Polar oils containing an ester group | Dibutyl adipate | — | 36.000 | 4.500 | 26.000 | 26.000 |
| | Propylheptylcaprylate | 4.000 | 6.000 | 4.000 | 4.000 | 4.000 |
| | Coco-caprylate/caprate | 36.000 | — | — | — | — |
| Oil without an ester group | Dimethicone | — | — | — | — | — |
| | C15-19 alkanes | — | — | — | — | — |
| | Octyldodecanol | — | — | — | — | — |
| Emulsifier | Polyglyceryl-4 isostearate | — | — | — | — | — |
| | Polyglyceryl-5 polyricinoleate | — | — | — | — | — |
| Sunscreen agent | Ethylhexylmethoxycinnamate | — | — | — | — | — |
| | Homosalate | — | — | — | — | — |
| | Diethylaminohydroxybenzoyl hexylbenzoate | — | — | — | — | — |
| | Octocrylene | — | — | — | — | — |
| Hectorite | Disteardimonium hectorite | 0.500 | 0.500 | 0.500 | 1.550 | 0.200 |
| Ratio of hector-ite:polar oil | | 1:80 | 1:84 | 1:17 | 1:19.4 | 1:150.0 |
| Purified water | Purified water (TO 100) | 53.900 | 51.900 | 85.400 | 62.850 | 64.200 |
| Moisturizer | Propanediol | 5.00 | 5.00 | 5.00 | 5.000 | 5.000 |
| Preser-vative | Caprylyl glycol | 0.1 | 0.1 | 0.1 | 0.1 | 0.1 |
| | Phenoxy ethanol | 0.500 | 0.500 | 0.500 | 0.500 | 0.500 |
| Formulation - emulsified or not (particle formation) | | ○ | ○ | ○ | ○ | ○ |
| Viscosity after shaking (LVT, No. 4*6 rpm) | | 6,500 | 2,000 | 20,000 | 32,500 | 800 |

The cosmetics of above Examples 1 to 10 include polar oils containing at least one ester group and organically modified clay minerals without a separate emulsifier, and it was confirmed that all cosmetics have particles formed, water drops are formed upon application after shaking to mix, and feeling of moisture and cool feeling are evaluated as excellent. In particular, the cosmetics of above Examples 1 to 6 include a specific weight ratio of polar oils containing at least one ester group and organically modified clay minerals, and showed more excellent feeling of moisture and cool feeling than Examples 7 to 10.

Example 2 includes a sunscreen agent ingredient as a skin active ingredient, and thus the content of other oil phase ingredients is partially adjusted.

TABLE 3

| | | Comparative Example | | | | | |
|---|---|---|---|---|---|---|---|
| | | 1 | 2 | 3 | 4 | 5 | 6 |
| Polar oils containing an ester group | Dibutyl adipate | 26.000 | 26.000 | 26.000 | — | — | — |
| | Propylheptylcaprylate | 4.000 | 4.000 | 4.000 | — | — | — |
| | Coco-caprylate/caprate | — | — | — | — | — | — |
| Oil without an ester group | Dimethicone | — | — | — | — | 30.000 | — |
| | C15-19 alkanes | — | — | — | 30.000 | — | — |
| | Octyldodecanol | — | — | — | — | — | 30.000 |

TABLE 3-continued

| | | Comparative Example | | | | | |
|---|---|---|---|---|---|---|---|
| | | 1 | 2 | 3 | 4 | 5 | 6 |
| Emulsifier | Polyglyceryl-4 isostearate | 2.000 | 0.500 | — | — | — | — |
| | Polyglyceryl-5 polyricinoleate | — | — | 2.000 | — | — | — |
| Sunscreen agent | Ethylhexylmethoxy-cinnamate | — | — | — | — | — | — |
| | Homosalate | — | — | — | — | — | — |
| | Diethylaminohydroxy-benzoylhexylbenzoate | — | — | — | — | — | — |
| | Octocrylene | — | — | — | — | — | — |
| Hectorite | Disteardimonium hectorite | 0.500 | 0.500 | 0.500 | 0.500 | 0.500 | 0.500 |
| Ratio of hectorite:polar oil | | 1:60 | 1:60 | 1:60 | 1:60 | 1:60 | 1:60 |
| Purified water | Purified water (TO 100) | 61.900 | 63.400 | 61.900 | 63.900 | 63.900 | 63.900 |
| Moisturizer | Propanediol | 5.00 | 5.00 | 5.00 | 5.00 | 5.00 | 5.00 |
| Preservative | Caprylyl glycol | 0.1 | 0.1 | 0.1 | 0.1 | 0.1 | 0.1 |
| | Phenoxy ethanol | 0.50 | 0.50 | 0.50 | 0.50 | 0.50 | 0.50 |
| Formulation - emulsified or not (particle formation) | | ○ | ○ | ○ | X1* | X2* | X3* |
| Viscosity after shaking (LVT, No. 4*6 rpm) | | 13,000 | 8,000 | 20,000 | X | 20,000 | 38,000 |

*X1: Fully separated within 10 seconds after emulsification without emulsified particles formed X2: Dispersible, without emulsified particles formed X3: Uneven size of emulsified particles with somewhat coalesced particles observed Difficult to shake due to too high viscosity with uneven distribution of aqueous phase particles How to Evaluate Feeling of Use In order to evaluate the feeling of use with respect to above Examples and Comparative Examples, thirty women in their 20s to 40s were presented with samples of Examples 1 to 10 and Comparative Examples 1 to 6 and were asked to relatively evaluate the same with a sensory test method. The feeling of use was evaluated after being divided into three items: feeling of moisture, cool feeling and water drop formation.

The evaluation results are shown in table 4 below.

Presence of water drops formed (Visual Evaluation)

The particle size of water drops is 1 mm to 3 mm: Very excellent ●

The particle size of water drops is 0.5 mm to less than 1 mm or greater than 5 mm: Excellent ○

The particle size of water drops is less than 0.5 mm or the water drop is not formed and cannot be identified with the naked eye: X Feeling of Moisture When applied to the skin, the feeling of moisture is very excellent-●, excellent-◑, average-○, No feeling of moisture-X Cool Feeling When applied to the skin, the cool feeling is very excellent-●, excellent-◑, average-○, no cool feeling-X

TABLE 4

| | Example | | | | | | | | | | Comparative Example | | | | | |
|---|---|---|---|---|---|---|---|---|---|---|---|---|---|---|---|---|
| | 1 | 2 | 3 | 4 | 5 | 6 | 7 | 8 | 9 | 10 | 1 | 2 | 3 | 4 | 5 | 6 |
| Presence of water drops formed | • | • | • | • | ○ | ○ | ○ | ○ | ○ | ○ | X | X | X | X | X | X |
| Feeling of moisture | • | • | ◑ | ◑ | ◑ | ○ | ○ | ○ | ○ | ○ | X | X | X | X | X | X |
| Cool feeling | • | • | ◑ | ◑ | ○ | ◑ | ○ | ○ | ○ | ○ | X | X | X | X | X | X |

In above Comparative Examples 1 to 3 containing an emulsifier, it was confirmed that no water drop is formed when the cosmetics are applied to the skin and the feeling of moisture and cool feeling are evaluated as poor.

In Comparative Examples 4 and 5 using non-polar oils (alkane oil or silicone oil) instead of polar oils containing at least one ester group used in the Examples of the present invention, it was confirmed that no emulsified particle is formed, no water drop is formed when the cosmetics are applied to the skin, and the feeling of moisture and cool feeling cannot be evaluated at all.

In Comparative Example 6 using polar oils (aliphatic alcohol) without an ester group instead of polar oils containing at least one ester group used in the Examples of the present invention, it was confirmed that some of the emulsified particles are observed, but aqueous particles are unevenly distributed with too high the viscosity, and water drops are finely formed when the cosmetics are applied to the skin, but the feeling of moisture and cool feeling are also evaluated as poor.

While specific portions of the present invention have been described in detail above, it is apparent to those skilled in the art that such detailed descriptions are set forth to illustrate exemplary embodiments only, but are not construed to limit the scope of the present invention. Thus, it should be understood that the substantial scope of the present invention is defined by the accompanying claims and equivalents thereto.

What is claimed is:

1. A water-in-oil cosmetic composition, comprising:

at least one skin active ingredient selected from the group consisting of idebenone, arbutin, and adenosine;

at least one organically modified clay mineral selected from the group consisting of quaternium-18 bentonite, quaternium-90 bentonite, and stearalkonium bentonite;

at least one polar oil containing at least one ester group, the polar oil being selected from the group consisting of dibutyl adipate, propylene glycol dicaprylate; C12-15 alkyl benzoate, propylheptyl caprylate, cetearyl isononanoate, butyloctyl salicylate, and diisopropyl adipate; and an aqueous phase comprising purified water, wherein a weight ratio of the organically modified clay mineral to the polar oil is from 1:20 to 1:80, wherein the water-in-oil cosmetic composition contains no added emulsifier, and is in a phase-separated state before shaking to mix and is transformed into a formulation having a viscosity of 3,000 to 25,000 CPS after shaking to mix.

* * * * *